US012575893B2

(12) United States Patent
Misener et al.

(10) Patent No.: US 12,575,893 B2
(45) Date of Patent: Mar. 17, 2026

(54) SHAPE SENSING FIBER OPTIC TIP PROTECTION SYSTEMS AND DEVICES

(71) Applicant: Bard Access Systems, Inc., Salt Lake City, UT (US)

(72) Inventors: Anthony K. Misener, Bountiful, UT (US); Steffan Sowards, Salt Lake City, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 130 days.

(21) Appl. No.: 17/849,447

(22) Filed: Jun. 24, 2022

(65) Prior Publication Data

US 2023/0417998 A1     Dec. 28, 2023

(51) Int. Cl.
*A61B 34/20*          (2016.01)
*A61B 1/07*           (2006.01)
(Continued)

(52) U.S. Cl.
CPC ................ *A61B 34/20* (2016.02); *A61B 1/07*
(2013.01); *A61B 5/065* (2013.01);
(Continued)

(58) Field of Classification Search
CPC ............ G02B 6/02057; G02B 6/02076; G02B
6/3624; G02B 6/241; G02B 6/02–0288;
(Continued)

(56) References Cited

U.S. PATENT DOCUMENTS

| 3,493,288 A | 2/1970 | Oltman et al. |
| 4,768,855 A | 9/1988 | Nishi et al. |

(Continued)

FOREIGN PATENT DOCUMENTS

| CA | 3025240 A1 | 11/2017 |
| DE | 102016109601 A1 | 11/2017 |

(Continued)

OTHER PUBLICATIONS

Kirill Bronnikov, Alexey Wolf, Sergey Yakushin, Alexandr Dostovalov, Olga Egorova, Sergey Zhuravlev, Sergey Semjonov, Stefan Wabnitz, and Sergey Babin, "Durable shape sensor based on FBG array inscribed in polyimide-coated multicore optical fiber," Opt. Express 27, 38421-38434 (2019). (Year: 2019).*

(Continued)

*Primary Examiner* — Daniel Petkovsek
(74) *Attorney, Agent, or Firm* — Rutan & Tucker LLP

(57)          ABSTRACT

Disclosed herein are fiber-optic assemblies for insertion within a patient body, that include an optical fiber and a secondary mechanical layer extending around a circumference of the optical fiber along at least the distal portion of the optical fiber. A distal tip section of the optical fiber includes a portion of the optical fiber disposed within a circuitous path, or an expansion of the optical fiber. The optical fiber may be a shape sensing optical fiber. A medical device assembly includes the fiber-optic assembly coupled with a catheter, a stylet, a probe, or a guidewire. The secondary mechanical layer and/or the expansion may be formed of an electrically conductive material.

12 Claims, 3 Drawing Sheets

(51) Int. Cl.
*A61B 5/06* (2006.01)
*G02B 6/02* (2006.01)
*G02B 6/36* (2006.01)

(52) U.S. Cl.
CPC ..... *G02B 6/02057* (2013.01); *G02B 6/02076* (2013.01); *A61B 2034/2046* (2016.02); *A61B 2034/2061* (2016.02); *G02B 6/3624* (2013.01)

(58) Field of Classification Search
CPC .. G02B 6/26; G02B 6/262; G02B 6/32; A61B 1/07; A61B 5/065; A61B 34/20; A61B 2034/2046; A61B 2034/2061
See application file for complete search history.

(56) References Cited

U.S. PATENT DOCUMENTS

| | | | |
|---|---|---|---|
| 4,777,955 A | | 10/1988 | Brayton et al. |
| 4,813,429 A | | 3/1989 | Eshel et al. |
| 4,898,176 A | | 2/1990 | Petre |
| 5,099,845 A | | 3/1992 | Besz et al. |
| 5,163,935 A | | 11/1992 | Black et al. |
| 5,178,153 A | * | 1/1993 | Einzig ................... G01L 11/025 |
| | | | 356/477 |
| 5,207,672 A | | 5/1993 | Roth et al. |
| 5,211,165 A | | 5/1993 | Dumoulin et al. |
| 5,220,703 A | | 6/1993 | Kanayama et al. |
| 5,275,151 A | | 1/1994 | Shockey et al. |
| 5,295,212 A | | 3/1994 | Morton et al. |
| 5,423,321 A | | 6/1995 | Fontenot |
| 5,454,807 A | | 10/1995 | Lennox et al. |
| 5,517,997 A | | 5/1996 | Fontenot |
| 5,599,492 A | | 2/1997 | Engelson |
| 5,622,170 A | | 4/1997 | Schulz |
| 5,633,494 A | * | 5/1997 | Danisch ............. G01D 5/35377 |
| | | | 250/227.16 |
| 5,693,043 A | * | 12/1997 | Kittrell .............. A61B 1/00096 |
| | | | 606/15 |
| 5,740,808 A | | 4/1998 | Panescu et al. |
| 5,827,313 A | | 10/1998 | Ream |
| 5,872,879 A | | 2/1999 | Hamm |
| 5,873,842 A | | 2/1999 | Brennen et al. |
| 5,879,306 A | | 3/1999 | Fontenot et al. |
| 5,906,579 A | | 5/1999 | Vander Salm et al. |
| 5,957,831 A | | 9/1999 | Adair |
| 6,035,229 A | | 3/2000 | Silverstein et al. |
| 6,069,698 A | | 5/2000 | Ozawa et al. |
| 6,081,741 A | | 6/2000 | Hollis |
| 6,178,346 B1 | | 1/2001 | Amundson et al. |
| 6,208,887 B1 | | 3/2001 | Clarke |
| 6,210,362 B1 | | 4/2001 | Ponzi |
| 6,319,227 B1 | | 11/2001 | Mansouri-Ruiz |
| 6,343,227 B1 | | 1/2002 | Crowley |
| 6,398,721 B1 | | 6/2002 | Nakamura et al. |
| 6,485,482 B1 | | 11/2002 | Belef |
| 6,563,105 B2 | | 5/2003 | Seibel et al. |
| 6,564,089 B2 | | 5/2003 | Izatt et al. |
| 6,593,884 B1 | | 7/2003 | Gilboa et al. |
| 6,597,941 B2 | | 7/2003 | Fontenot et al. |
| 6,619,857 B2 | | 9/2003 | Miyake |
| 6,650,923 B1 | | 11/2003 | Lesh et al. |
| 6,685,666 B1 | | 2/2004 | Fontenot |
| 6,687,010 B1 | | 2/2004 | Horii et al. |
| 6,690,966 B1 | | 2/2004 | Rava et al. |
| 6,701,181 B2 | | 3/2004 | Tang et al. |
| 6,711,426 B2 | | 3/2004 | Benaron et al. |
| 6,816,743 B2 | | 11/2004 | Moreno et al. |
| 6,892,090 B2 | | 5/2005 | Verard et al. |
| 6,895,267 B2 | | 5/2005 | Panescu et al. |
| 6,975,803 B2 | | 12/2005 | Koide et al. |
| 7,043,287 B1 | | 5/2006 | Khalil et al. |
| 7,132,645 B2 | | 11/2006 | Kom |
| 7,273,056 B2 | | 9/2007 | Wilson et al. |
| 7,344,533 B2 | | 3/2008 | Pearson et al. |
| 7,366,562 B2 | | 4/2008 | Dukesherer et al. |
| 7,366,563 B2 | | 4/2008 | Kleen et al. |
| 7,396,354 B2 | | 7/2008 | Rychnovsky et al. |
| 7,406,346 B2 | | 7/2008 | Kleen et al. |
| 7,515,265 B2 | | 4/2009 | Alfano et al. |
| 7,532,920 B1 | | 5/2009 | Ainsworth et al. |
| 7,587,236 B2 | | 9/2009 | Demos et al. |
| 7,603,166 B2 | | 10/2009 | Casscells et al. |
| 7,699,855 B2 | | 4/2010 | Anderson et al. |
| 7,729,735 B1 | | 6/2010 | Burchman |
| 7,757,695 B2 | | 7/2010 | Wilson et al. |
| 7,758,499 B2 | | 7/2010 | Adler |
| 7,840,253 B2 | | 11/2010 | Tremblay et al. |
| 7,992,573 B2 | | 8/2011 | Wilson et al. |
| 8,032,200 B2 | | 10/2011 | Tearney et al. |
| 8,054,469 B2 | | 11/2011 | Nakabayashi et al. |
| 8,060,187 B2 | | 11/2011 | Marshik-Geurts et al. |
| 8,073,517 B1 | | 12/2011 | Burchman |
| 8,078,261 B2 | | 12/2011 | Imam |
| 8,182,433 B2 | | 5/2012 | Leo et al. |
| 8,187,189 B2 | | 5/2012 | Jung et al. |
| 8,197,494 B2 | | 6/2012 | Jaggi et al. |
| 8,267,932 B2 | | 9/2012 | Baxter et al. |
| 8,369,932 B2 | | 2/2013 | Cinbis et al. |
| 8,388,541 B2 | | 3/2013 | Messerly et al. |
| 8,571,640 B2 | | 10/2013 | Holman |
| 8,597,315 B2 | | 12/2013 | Snow et al. |
| 8,622,935 B1 | | 1/2014 | Leo |
| 8,700,358 B1 | | 4/2014 | Parker, Jr. |
| 8,781,555 B2 | | 7/2014 | Burnside et al. |
| 8,798,721 B2 | | 8/2014 | Dib |
| 8,968,331 B1 | | 3/2015 | Sochor |
| 8,979,871 B2 | | 3/2015 | Tyc et al. |
| 9,119,551 B2 | | 9/2015 | Qi et al. |
| 9,186,046 B2 | | 11/2015 | Ramamurthy et al. |
| 9,339,206 B2 | | 5/2016 | Grunwald |
| 9,339,221 B1 | | 5/2016 | Heaton et al. |
| 9,345,510 B2 | * | 5/2016 | Patel .................. A61B 1/00183 |
| 9,360,630 B2 | | 6/2016 | Jenner et al. |
| 9,549,685 B2 | | 1/2017 | Cox et al. |
| 9,560,954 B2 | | 2/2017 | Jacobs et al. |
| 9,572,492 B2 | * | 2/2017 | Simpson ................ A61B 90/39 |
| 9,622,706 B2 | | 4/2017 | Dick et al. |
| 9,645,326 B1 | | 5/2017 | Sausse et al. |
| 9,649,048 B2 | | 5/2017 | Cox et al. |
| 9,678,275 B1 | | 6/2017 | Griffin |
| 9,678,284 B2 | | 6/2017 | Coggi et al. |
| 9,737,213 B1 | | 8/2017 | Heaton et al. |
| 9,872,978 B1 | | 1/2018 | Zaborsky et al. |
| 10,231,643 B2 | | 3/2019 | Grunwald |
| 10,231,753 B2 | | 3/2019 | Burnside et al. |
| 10,258,240 B1 | | 4/2019 | Eberle et al. |
| 10,265,133 B1 | | 4/2019 | McClellan |
| 10,327,830 B2 | | 6/2019 | Grant et al. |
| 10,349,890 B2 | | 7/2019 | Misener et al. |
| 10,448,837 B2 | | 10/2019 | Manzke et al. |
| 10,492,876 B2 | | 12/2019 | Anastassiou et al. |
| 10,551,245 B2 | | 2/2020 | Do et al. |
| 10,568,586 B2 | | 2/2020 | Begin et al. |
| 10,603,126 B2 | | 3/2020 | Karguth et al. |
| 10,620,386 B2 | | 4/2020 | Van Der Mark et al. |
| 10,631,718 B2 | | 4/2020 | Petroff et al. |
| 10,687,891 B2 | | 6/2020 | Belhe et al. |
| 10,932,670 B2 | * | 3/2021 | Smith .................. A61B 5/0066 |
| 10,939,889 B2 | | 3/2021 | Flexman et al. |
| 10,992,078 B2 | | 4/2021 | Thompson et al. |
| 10,992,079 B2 | | 4/2021 | Stats et al. |
| 11,000,207 B2 | | 5/2021 | Burnside et al. |
| 11,000,265 B1 | | 5/2021 | Ryu et al. |
| 11,103,321 B2 | | 8/2021 | Braun et al. |
| 11,123,047 B2 | | 9/2021 | Jaffer et al. |
| 11,259,892 B2 | | 3/2022 | Hufford et al. |
| 11,284,916 B2 | * | 3/2022 | Patel .................. A61M 25/1011 |
| 11,369,342 B2 | | 6/2022 | Irisawa |
| 11,382,653 B2 | * | 7/2022 | Patel .................. A61B 1/00183 |
| 11,474,310 B2 | | 10/2022 | Sowards et al. |
| 11,525,670 B2 | | 12/2022 | Messerly et al. |
| 11,547,282 B2 | | 1/2023 | Weise et al. |
| 11,607,150 B2 | | 3/2023 | Schweikert et al. |
| 11,621,518 B2 | | 4/2023 | Stats et al. |

(56) References Cited

U.S. PATENT DOCUMENTS

| | | | |
|---|---|---|---|
| 11,630,009 B2 | 4/2023 | Misener et al. | |
| 11,707,205 B2 | 7/2023 | Messerly et al. | |
| 11,806,096 B2 | 11/2023 | Flatt et al. | |
| 11,850,073 B2* | 12/2023 | Wright | A61B 5/6885 |
| 11,931,112 B2 | 3/2024 | Thompson et al. | |
| 12,038,338 B2 | 7/2024 | Misener et al. | |
| 12,048,478 B2 | 7/2024 | Tegg et al. | |
| 12,089,815 B2* | 9/2024 | Sowards | A61B 1/00043 |
| 2002/0019627 A1 | 2/2002 | Maguire et al. | |
| 2002/0087206 A1 | 7/2002 | Hirschberg et al. | |
| 2002/0166190 A1 | 11/2002 | Miyake et al. | |
| 2002/0188285 A1 | 12/2002 | Brown | |
| 2002/0198457 A1 | 12/2002 | Tearney et al. | |
| 2003/0045798 A1* | 3/2003 | Hular | A61B 5/6848 |
| | | | 600/476 |
| 2003/0092995 A1 | 5/2003 | Thompson | |
| 2004/0039274 A1 | 2/2004 | Benaron et al. | |
| 2004/0111020 A1 | 6/2004 | Long | |
| 2004/0111147 A1 | 6/2004 | Rabkin et al. | |
| 2004/0242995 A1 | 12/2004 | Maschke | |
| 2004/0247268 A1 | 12/2004 | Ishihara et al. | |
| 2004/0260182 A1 | 12/2004 | Zuluaga et al. | |
| 2005/0033264 A1 | 2/2005 | Redinger | |
| 2005/0113719 A1 | 5/2005 | Saadat | |
| 2005/0272975 A1 | 12/2005 | McWeeney et al. | |
| 2006/0013523 A1 | 1/2006 | Childers et al. | |
| 2006/0030753 A1 | 2/2006 | Boutillette et al. | |
| 2006/0036164 A1 | 2/2006 | Wilson et al. | |
| 2006/0069305 A1 | 3/2006 | Couvillon et al. | |
| 2006/0100610 A1 | 5/2006 | Wallace et al. | |
| 2006/0189959 A1 | 8/2006 | Schneiter | |
| 2006/0200049 A1 | 9/2006 | Leo et al. | |
| 2006/0241395 A1 | 10/2006 | Kruger et al. | |
| 2006/0241492 A1 | 10/2006 | Boese et al. | |
| 2007/0060847 A1 | 3/2007 | Leo et al. | |
| 2007/0156019 A1 | 7/2007 | Larkin et al. | |
| 2007/0179485 A1 | 8/2007 | Yeik et al. | |
| 2007/0201793 A1 | 8/2007 | Askins et al. | |
| 2007/0225563 A1 | 9/2007 | Ogino | |
| 2007/0253673 A1 | 11/2007 | Nielsen et al. | |
| 2007/0265503 A1 | 11/2007 | Schlesinger et al. | |
| 2007/0287886 A1 | 12/2007 | Saadat | |
| 2007/0299425 A1 | 12/2007 | Waner et al. | |
| 2008/0034519 A1 | 2/2008 | Fujiwara | |
| 2008/0172119 A1 | 7/2008 | Yamasaki et al. | |
| 2008/0183128 A1 | 7/2008 | Morriss et al. | |
| 2008/0281293 A1 | 11/2008 | Peh et al. | |
| 2008/0285909 A1 | 11/2008 | Younge et al. | |
| 2009/0005675 A1 | 1/2009 | Grunwald et al. | |
| 2009/0018393 A1 | 1/2009 | Dick et al. | |
| 2009/0046980 A1 | 2/2009 | Rohlen | |
| 2009/0062634 A1 | 3/2009 | Say et al. | |
| 2009/0137952 A1 | 5/2009 | Ramamurthy et al. | |
| 2009/0208143 A1* | 8/2009 | Yoon | A61B 5/0062 |
| | | | 382/312 |
| 2009/0227992 A1 | 9/2009 | Nir et al. | |
| 2009/0234328 A1 | 9/2009 | Cox et al. | |
| 2009/0253967 A1 | 10/2009 | Gill et al. | |
| 2009/0270729 A1 | 10/2009 | Corbucci et al. | |
| 2009/0304582 A1 | 12/2009 | Rousso et al. | |
| 2009/0318757 A1 | 12/2009 | Singh | |
| 2009/0324161 A1 | 12/2009 | Prisco | |
| 2010/0016729 A1 | 1/2010 | Futrell | |
| 2010/0030063 A1 | 2/2010 | Lee et al. | |
| 2010/0063534 A1 | 3/2010 | Kugler et al. | |
| 2010/0114115 A1 | 5/2010 | Schlesinger et al. | |
| 2010/0114190 A1 | 5/2010 | Bendett et al. | |
| 2010/0139669 A1 | 6/2010 | Piferi et al. | |
| 2010/0204569 A1 | 8/2010 | Burnside et al. | |
| 2010/0286531 A1 | 11/2010 | Ryan et al. | |
| 2010/0292758 A1 | 11/2010 | Lee et al. | |
| 2011/0087112 A1 | 4/2011 | Leo et al. | |
| 2011/0098533 A1 | 4/2011 | Onoda et al. | |
| 2011/0144481 A1 | 6/2011 | Feer et al. | |
| 2011/0144630 A1 | 6/2011 | Loeb | |
| 2011/0166442 A1 | 7/2011 | Sarvazyan | |
| 2011/0172680 A1 | 7/2011 | Younge et al. | |
| 2011/0178509 A1* | 7/2011 | Zerfas | G02B 6/02395 |
| | | | 606/2.5 |
| 2011/0196248 A1 | 8/2011 | Grunwald | |
| 2011/0245662 A1 | 10/2011 | Eggers et al. | |
| 2011/0295108 A1 | 12/2011 | Cox et al. | |
| 2012/0046562 A1 | 2/2012 | Powers et al. | |
| 2012/0116161 A1 | 5/2012 | Nieman et al. | |
| 2012/0143029 A1 | 6/2012 | Silverstein et al. | |
| 2012/0184827 A1 | 7/2012 | Shwartz et al. | |
| 2012/0184955 A1 | 7/2012 | Pivotto et al. | |
| 2012/0321243 A1 | 12/2012 | Younge et al. | |
| 2013/0096482 A1 | 4/2013 | Bertrand et al. | |
| 2013/0104884 A1 | 5/2013 | Vazales et al. | |
| 2013/0150732 A1 | 6/2013 | Manzke et al. | |
| 2013/0188855 A1 | 7/2013 | Desjardins et al. | |
| 2013/0190741 A1 | 7/2013 | Moll et al. | |
| 2013/0204124 A1 | 8/2013 | Duindam et al. | |
| 2013/0211246 A1 | 8/2013 | Parasher | |
| 2013/0296652 A1 | 11/2013 | Farr | |
| 2013/0296693 A1 | 11/2013 | Wenzel et al. | |
| 2013/0310668 A1 | 11/2013 | Young | |
| 2013/0324840 A1 | 12/2013 | Zhongping et al. | |
| 2014/0031674 A1 | 1/2014 | Newman et al. | |
| 2014/0046261 A1 | 2/2014 | Newman et al. | |
| 2014/0058368 A1* | 2/2014 | Hogue | A61B 18/22 |
| | | | 606/16 |
| 2014/0073950 A1 | 3/2014 | Akui et al. | |
| 2014/0088413 A1 | 3/2014 | Von Bucsh et al. | |
| 2014/0121468 A1 | 5/2014 | Eichenholz | |
| 2014/0155948 A1 | 6/2014 | Walsh et al. | |
| 2014/0180087 A1 | 6/2014 | Millett et al. | |
| 2014/0188133 A1 | 7/2014 | Misener | |
| 2014/0221829 A1 | 8/2014 | Maitland et al. | |
| 2014/0259477 A1 | 9/2014 | Huang | |
| 2014/0268167 A1 | 9/2014 | Friedman et al. | |
| 2014/0275997 A1 | 9/2014 | Chopra et al. | |
| 2014/0318825 A1 | 10/2014 | Erb et al. | |
| 2014/0323887 A1 | 10/2014 | Anderson et al. | |
| 2014/0378945 A1 | 12/2014 | Beri | |
| 2015/0029511 A1 | 1/2015 | 'T Hooft et al. | |
| 2015/0031987 A1 | 1/2015 | Pameijer et al. | |
| 2015/0045649 A1 | 2/2015 | O'Dea et al. | |
| 2015/0080688 A1 | 3/2015 | Cinbis et al. | |
| 2015/0099979 A1 | 4/2015 | Caves et al. | |
| 2015/0105654 A1* | 4/2015 | Meyer | A61B 1/3137 |
| | | | 600/300 |
| 2015/0119700 A1 | 4/2015 | Liang et al. | |
| 2015/0119724 A1 | 4/2015 | Weber et al. | |
| 2015/0209113 A1 | 7/2015 | Burkholz et al. | |
| 2015/0209117 A1 | 7/2015 | Flexman et al. | |
| 2015/0244465 A1 | 8/2015 | Chou et al. | |
| 2015/0270900 A1 | 9/2015 | Hilario et al. | |
| 2015/0272445 A1 | 10/2015 | Rozental et al. | |
| 2015/0301288 A1 | 10/2015 | Thornton, Jr. | |
| 2015/0305816 A1 | 10/2015 | Hadzic | |
| 2015/0320977 A1 | 11/2015 | Vitullo et al. | |
| 2016/0018602 A1 | 1/2016 | Govari et al. | |
| 2016/0151115 A1 | 6/2016 | Karguth et al. | |
| 2016/0166326 A1 | 6/2016 | Bakker et al. | |
| 2016/0166341 A1 | 6/2016 | Iordachita et al. | |
| 2016/0184020 A1 | 6/2016 | Kowalewski et al. | |
| 2016/0256228 A1 | 9/2016 | Haartsen et al. | |
| 2016/0262627 A1* | 9/2016 | Hecker | A61B 5/205 |
| 2016/0302762 A1 | 10/2016 | Stigall et al. | |
| 2016/0331360 A1 | 11/2016 | Hera et al. | |
| 2016/0354038 A1 | 12/2016 | Demirtas et al. | |
| 2016/0357007 A1 | 12/2016 | Swanson | |
| 2016/0374589 A1 | 12/2016 | Misener et al. | |
| 2017/0017048 A1 | 1/2017 | Coggi et al. | |
| 2017/0020394 A1 | 1/2017 | Harrington | |
| 2017/0052091 A1 | 2/2017 | Mori | |
| 2017/0079548 A1 | 3/2017 | Silverstein et al. | |
| 2017/0082806 A1 | 3/2017 | Van Der Mark et al. | |
| 2017/0196479 A1 | 7/2017 | Liu et al. | |
| 2017/0201036 A1 | 7/2017 | Cohen et al. | |
| 2017/0215973 A1 | 8/2017 | Flexman et al. | |
| 2017/0231699 A1 | 8/2017 | Flexman et al. | |

(56) References Cited

U.S. PATENT DOCUMENTS

| | | |
|---|---|---|
| 2017/0273542 A1 | 9/2017 | Au |
| 2017/0273565 A1 | 9/2017 | Ma et al. |
| 2017/0273628 A1 | 9/2017 | Ofek et al. |
| 2017/0290542 A1 | 10/2017 | Chandrasoma |
| 2017/0296037 A1 | 10/2017 | Yoshino |
| 2017/0303824 A1 | 10/2017 | Schlesinger et al. |
| 2017/0311924 A1* | 11/2017 | Sudol ................... A61B 8/4254 |
| 2017/0333136 A1 | 11/2017 | Hladio et al. |
| 2017/0348063 A1 | 12/2017 | Braun et al. |
| 2018/0067268 A1 | 3/2018 | Murakami et al. |
| 2018/0093078 A1 | 4/2018 | Patil et al. |
| 2018/0095231 A1 | 4/2018 | Lowell et al. |
| 2018/0113038 A1 | 4/2018 | Janabi-Sharifi et al. |
| 2018/0116551 A1 | 5/2018 | Newman et al. |
| 2018/0140170 A1 | 5/2018 | Van Putten et al. |
| 2018/0175547 A1 | 6/2018 | Hsu |
| 2018/0239124 A1 | 8/2018 | Naruse et al. |
| 2018/0250088 A1 | 9/2018 | Brennan et al. |
| 2018/0264227 A1 | 9/2018 | Flexman et al. |
| 2018/0289243 A1 | 10/2018 | Landey et al. |
| 2018/0289390 A1 | 10/2018 | Amorizzo et al. |
| 2018/0289927 A1 | 10/2018 | Messerly |
| 2018/0317751 A1 | 11/2018 | Kuboi et al. |
| 2018/0339134 A1 | 11/2018 | Leo |
| 2018/0360545 A1 | 12/2018 | Cole et al. |
| 2018/0369432 A1 | 12/2018 | Zaborsky |
| 2019/0008376 A1 | 1/2019 | Wortelboer et al. |
| 2019/0059743 A1 | 2/2019 | Ramachandran et al. |
| 2019/0110838 A1 | 4/2019 | Martinez et al. |
| 2019/0110839 A1 | 4/2019 | Rafii-Tari et al. |
| 2019/0110844 A1 | 4/2019 | Misener et al. |
| 2019/0142528 A1* | 5/2019 | Vertikov ............ A61B 1/00172<br>600/424 |
| 2019/0192818 A1 | 6/2019 | Koda et al. |
| 2019/0212761 A1* | 7/2019 | Swanson .............. A61B 5/0075 |
| 2019/0223706 A1 | 7/2019 | Takeuchi et al. |
| 2019/0235182 A1 | 8/2019 | Cheng |
| 2019/0237902 A1 | 8/2019 | Thompson et al. |
| 2019/0271815 A1 | 9/2019 | Van Der Mark et al. |
| 2019/0321110 A1 | 10/2019 | Grunwald et al. |
| 2019/0343424 A1 | 11/2019 | Blumenkranz et al. |
| 2019/0357875 A1 | 11/2019 | Qi et al. |
| 2019/0374196 A1 | 12/2019 | Courtney et al. |
| 2020/0022587 A1 | 1/2020 | Glover et al. |
| 2020/0046434 A1 | 2/2020 | Graetzel et al. |
| 2020/0060718 A1* | 2/2020 | Patel ................... A61B 5/6852 |
| 2020/0069192 A1 | 3/2020 | Sanborn et al. |
| 2020/0093353 A1 | 3/2020 | Tezuka et al. |
| 2020/0155073 A1 | 5/2020 | Hwang et al. |
| 2020/0170724 A1 | 6/2020 | Flatt et al. |
| 2020/0188036 A1 | 6/2020 | Ding et al. |
| 2020/0238051 A1 | 7/2020 | Hwang et al. |
| 2020/0261720 A1 | 8/2020 | Danitz et al. |
| 2020/0275827 A1 | 9/2020 | Weise et al. |
| 2020/0305983 A1 | 10/2020 | Yampolsky et al. |
| 2021/0007796 A1* | 1/2021 | Panescu ................. A61B 34/20 |
| 2021/0030504 A1 | 2/2021 | Thompson et al. |
| 2021/0045814 A1 | 2/2021 | Thompson et al. |
| 2021/0113274 A1* | 4/2021 | Bydlon ................. G01B 11/24 |
| 2021/0154440 A1 | 5/2021 | Misener |
| 2021/0156676 A1* | 5/2021 | Messerly ............ G01B 11/161 |
| 2021/0205585 A1 | 7/2021 | Ullmann et al. |
| 2021/0215871 A1 | 7/2021 | Hayes et al. |
| 2021/0268229 A1 | 9/2021 | Sowards et al. |
| 2021/0271035 A1 | 9/2021 | Sowards et al. |
| 2021/0275256 A1 | 9/2021 | Sowards et al. |
| 2021/0275257 A1 | 9/2021 | Prior et al. |
| 2021/0278604 A1 | 9/2021 | Rohr Daniel et al. |
| 2021/0282867 A1 | 9/2021 | Tegg et al. |
| 2021/0290315 A1 | 9/2021 | Lampert et al. |
| 2021/0298680 A1 | 9/2021 | Sowards et al. |
| 2021/0299879 A1 | 9/2021 | Pinter et al. |
| 2021/0325172 A1 | 10/2021 | Hendriks et al. |
| 2021/0330398 A1* | 10/2021 | Tegg ................... A61B 34/20 |
| 2021/0389519 A1 | 12/2021 | Choi et al. |
| 2021/0401456 A1 | 12/2021 | Cox et al. |
| 2021/0401509 A1 | 12/2021 | Misener et al. |
| 2021/0402144 A1 | 12/2021 | Messerly |
| 2022/0034733 A1 | 2/2022 | Misener et al. |
| 2022/0039632 A1 | 2/2022 | Polejaev et al. |
| 2022/0039744 A1 | 2/2022 | Koenig |
| 2022/0110695 A1 | 4/2022 | Sowards et al. |
| 2022/0110706 A1 | 4/2022 | Misener et al. |
| 2022/0133401 A1 | 5/2022 | O'Brien et al. |
| 2022/0152349 A1 | 5/2022 | Sowards et al. |
| 2022/0160209 A1 | 5/2022 | Sowards et al. |
| 2022/0188285 A1 | 6/2022 | Ofenloch |
| 2022/0257975 A1 | 8/2022 | Croll et al. |
| 2022/0330891 A1 | 10/2022 | Sowards et al. |
| 2022/0361762 A1 | 11/2022 | Lalancette et al. |
| 2023/0082991 A1 | 3/2023 | Sowards et al. |
| 2023/0149080 A1 | 5/2023 | Wong et al. |
| 2023/0285085 A1 | 9/2023 | Misener et al. |
| 2023/0292997 A1* | 9/2023 | Sowards .............. A61B 5/6853<br>600/182 |
| 2023/0293243 A1 | 9/2023 | Sowards et al. |
| 2023/0320663 A1 | 10/2023 | Misener et al. |
| 2023/0338090 A1 | 10/2023 | Misener et al. |
| 2023/0346314 A1 | 11/2023 | Sowards et al. |
| 2023/0346482 A1 | 11/2023 | Sowards et al. |
| 2023/0379057 A1 | 11/2023 | Moore |
| 2023/0414293 A1* | 12/2023 | Farley ................... A61B 34/20 |
| 2024/0016425 A1 | 1/2024 | Sowards et al. |
| 2024/0094475 A1 | 3/2024 | Misener et al. |
| 2024/0180470 A1 | 6/2024 | Sowards et al. |
| 2024/0215917 A1 | 7/2024 | Sowards et al. |
| 2024/0423456 A1 | 12/2024 | Sowards et al. |
| 2025/0176853 A1 | 6/2025 | Sowards et al. |
| 2025/0186134 A1 | 6/2025 | Sowards et al. |
| 2025/0249208 A1 | 8/2025 | Sowards et al. |
| 2025/0288366 A1 | 9/2025 | Misener et al. |

FOREIGN PATENT DOCUMENTS

| | | | |
|---|---|---|---|
| EP | 2240111 A2 | 10/2010 | |
| EP | 2385802 B1 | 8/2013 | |
| EP | 3266383 A1 | 1/2018 | |
| EP | 2809249 B1 * | 12/2018 | ......... A61B 17/3468 |
| EP | 3545849 A1 | 10/2019 | |
| EP | 3725252 A1 | 10/2020 | |
| WO | 99/64099 A1 | 12/1999 | |
| WO | 2006080076 A1 | 8/2006 | |
| WO | 2006122001 A2 | 11/2006 | |
| WO | 2009/155325 A2 | 12/2009 | |
| WO | 2011141830 A1 | 11/2011 | |
| WO | 2011150376 A1 | 12/2011 | |
| WO | 2012064769 A2 | 5/2012 | |
| WO | 2012135339 A1 | 10/2012 | |
| WO | WO-2013114376 A1 * | 8/2013 | ............ A61B 18/22 |
| WO | 2014049555 A1 | 4/2014 | |
| WO | 2015055413 A1 | 4/2015 | |
| WO | 2015074045 A2 | 5/2015 | |
| WO | 2016/061431 A1 | 4/2016 | |
| WO | 2016193051 A1 | 12/2016 | |
| WO | 2018071490 A1 | 4/2018 | |
| WO | 2018/096491 A1 | 5/2018 | |
| WO | 2019037071 A1 | 2/2019 | |
| WO | 2019/046769 A1 | 3/2019 | |
| WO | 2019020713 A1 | 12/2019 | |
| WO | 2020/142470 A1 | 7/2020 | |
| WO | 2021021408 A1 | 2/2021 | |
| WO | 2021030092 A1 | 2/2021 | |
| WO | 2021108688 A1 | 6/2021 | |
| WO | 2021108697 A1 | 6/2021 | |
| WO | 2021144317 A1 | 7/2021 | |
| WO | 2021178578 A1 | 9/2021 | |
| WO | 2022/031613 A1 | 2/2022 | |
| WO | 2022/081586 A1 | 4/2022 | |
| WO | 2022/081723 A1 | 4/2022 | |
| WO | 2022109045 A1 | 5/2022 | |
| WO | 2022115624 A1 | 6/2022 | |
| WO | 2022221608 A1 | 10/2022 | |
| WO | 2023043947 A1 | 3/2023 | |
| WO | 2023172652 A1 | 9/2023 | |

(56)                    References Cited

FOREIGN PATENT DOCUMENTS

| WO | 2023177822 A1 | 9/2023 |
| WO | 2023177889 A1 | 9/2023 |
| WO | 2023200734 A1 | 10/2023 |
| WO | 2023205257 A1 | 10/2023 |
| WO | 2023212096 A1 | 11/2023 |
| WO | 2023212098 A1 | 11/2023 |
| WO | 2023249952 A1 | 12/2023 |
| WO | 2024015464 A1 | 1/2024 |
| WO | 2024123837 A1 | 6/2024 |

OTHER PUBLICATIONS

PCT/US2023/014849 filed Mar. 8, 2023 International Search Report and Written Opinion dated Jun. 7, 2023.
PCT/US2023/015536 filed Mar. 17, 2023 International Search Report and Written Opinion dated Jun. 22, 2023.
PCT/US2023/018076 filed Apr. 10, 2023 International Search Report and Written Opinion dated Jul. 11, 2023.
PCT/US2023/019130 filed Apr. 19, 2023 International Search Report and Written Opinion dated Jul. 19, 2023.
PCT/US2023/020044 filed Apr. 26, 2023 International Search Report and Written Opinion dated Jul. 19, 2023.
U.S. Appl. No. 17/217,852, filed Mar. 30, 2021 Ex Parte Quayle Action dated Sep. 8, 2023.
U.S. Appl. No. 17/499,644, filed Oct. 12, 2021 Restriction Requirement dated Jul. 11, 2023.
U.S. Appl. No. 17/697,895, filed Mar. 17, 2022 Advisory Action dated Sep. 8, 2023.
U.S. Appl. No. 17/697,895, filed Mar. 17, 2022 Final Office Action dated Aug. 16, 2023.
U.S. Appl. No. 17/697,895, filed Mar. 17, 2022 Non Final Office Action dated Jun. 14, 2023.
U.S. Appl. No. 17/187,536, filed Feb. 26, 2021 Non-Final Office Action dated Dec. 15, 2023.
U.S. Appl. No. 17/535,406, filed Nov. 24, 2021 Non-Final Office Action dated Feb. 15, 2024.
U.S. Appl. No. 17/689,773, filed Mar. 8, 2022 Non-Final Office Action dated Mar. 19, 2024.
U.S. Appl. No. 17/697,895, filed Mar. 17, 2022 Non-Final Office Action dated Jan. 11, 2024.
U.S. Appl. No. 17/731,155, filed Apr. 27, 2022 Restriction Requirement dated Feb. 28, 2024.
PCT/US2022/024934 filed Apr. 14, 2022 International Search Report and Written Opinion dated Jul. 18. 2022.
PCT/US2023/020042 filed Apr. 26, 2023 International Search Report and Written Opinion dated Sep. 26, 2023.
PCT/US2023/025757 filed Jun. 20, 2023 International Search Report and Written Opinion dated Sep. 11, 2023.
PCT/US2023/027527 filed Jul. 12, 2023 International Search Report and Written Opinion dated Oct. 16, 2023.
U.S. Appl. No. 17/187,536, filed Feb. 26, 2021 Advisory Action dated Nov. 21, 2023.
U.S. Appl. No. 17/187,536, filed Feb. 26, 2021 Final Office Action dated Sep. 20, 2023.
U.S. Appl. No. 17/217,852, filed Mar. 30, 2021 Notice of Allowance dated Nov. 7, 2023.
U.S. Appl. No. 17/499,644, filed Oct. 12, 2021 Notice of Allowance dated Sep. 18, 2023.
U.S. Appl. No. 17/535,406, filed Nov. 24, 2021 Restriction Requirement dated Nov. 24, 2023.
PCT/US2022/043698 filed Sep. 15, 2022 International Search Report and Written Opinion dated Dec. 19. 2022.
U.S. Appl. No. 17/967,794, filed Oct. 17, 2022 Notice of Allowance dated Feb. 15, 2023.
PCT/US2021 /059755 filed Nov. 17, 2021 International Search Report and Written Opinion dated Apr. 29, 2022.
PCT/US2021/019713 filed Feb. 25, 2021 International Search Report and Written Opinion dated Jul. 6, 2021.

PCT/US2021/020079 filed Feb. 26, 2021 International Search Report and Written Opinion dated Jun. 4, 2021.
PCT/US2021/020732 filed Mar. 3, 2021 International Search Report and Written Opinion dated Jul. 5, 2021.
PCT/US2021/060849 filed Nov. 24, 2021 International Search Report and Written Opinion dated Mar. 9, 2022.
U.S. Appl. No. 17/185,777, filed Feb. 25, 2021 Non-Final Office Action dated Feb. 9, 2022.
U.S. Appl. No. 17/185,777, filed Feb. 25, 2021 Notice of Allowance dated Jun. 10, 2022.
PCT/US2021/024969 filed Mar. 30, 2021 International Search Report and Written Opinion dated Jul. 19, 2021.
PCT/US2021/054596 filed Oct. 12, 2021 International Search Report and Written Opinion dated Jan. 26, 2022.
U.S. Appl. No. 17/217,852, filed Mar. 30, 2021 Non Final Office Action dated Jun. 7, 2023.
U.S. Appl. No. 17/217,852, filed Mar. 30, 2021 Restriction Requirement dated Mar. 21, 2023.
PCT/US2023/015416 filed Mar. 16, 2023 International Search Report and Written Opinion dated May 26, 2023.
U.S. Appl. No. 17/187,536, filed Feb. 26, 2021 Non-Final Office Action dated May 17, 2023.
PCT/US2022/043698 filed Sep. 15, 2022 International Preliminary Report on Patentability dated Mar. 5, 2024.
PCT/US2023/082605 filed Dec. 5, 2023 International Search Report and Written Opinion dated Feb. 28, 2024.
U.S. Appl. No. 17/187,536, filed Feb. 26, 2021 Final Office Action dated Jul. 2, 2024.
U.S. Appl. No. 17/696,675, filed Mar. 16, 2022 Non-Final Office Action dated Jun. 11, 2024.
U.S. Appl. No. 17/697,895, filed Mar. 17, 2022 Notice of Allowance dated May 8, 2024.
U.S. Appl. No. 17/725,394, filed Apr. 20, 2022 Non-Final Office Action dated Jun. 17, 2024.
U.S. Appl. No. 18/524,620, filed Nov. 30, 2023 Non-Final Office Action dated Jun. 18, 2024.
PCT/US2023/018076 filed Apr. 10, 2023 International Preliminary Report on Patentability dated Oct. 8, 2024.
PCT/US2023/019130 filed Apr. 19, 2023 International Preliminary Report on Patentability dated Oct. 8, 2024.
PCT/US2023/020044 filed Apr. 26, 2023 International Preliminary Report on Patentability dated Oct. 29, 2024.
U.S. Appl. No. 17/187,536, filed Feb. 26, 2021 Advisory Action dated Oct. 9, 2024.
U.S. Appl. No. 17/187,536, filed Feb. 26, 2021 Notice of Allowance dated Oct. 29, 2024.
U.S. Appl. No. 17/191,551, filed Mar. 3, 2021 Notice of Allowance dated Nov. 8, 2024.
U.S. Appl. No. 17/535,406, filed Nov. 24, 2021 Notice of Allowance dated Oct. 23, 2024.
U.S. Appl. No. 17/689,773, filed Mar. 8, 2022 Advisory Action dated Nov. 1, 2024.
U.S. Appl. No. 17/696,675, filed Mar. 16, 2022 Final Office Action dated Dec. 5, 2024.
U.S. Appl. No. 17/725,394, filed Apr. 20, 2022 Non-Final Office Action dated Nov. 19, 2024.
U.S. Appl. No. 17/863,211, filed Jul. 12, 2022 Restriction Requirement dated Nov. 15, 2024.
PCT/US2023/015536 filed Mar. 17, 2023 International Preliminary Report on Patentability dated Sep. 10, 2024.
U.S. Appl. No. 17/191,551, filed Mar. 3, 2021 Non-Final Office Action dated Aug. 16, 2024.
U.S. Appl. No. 17/529,022, filed Nov. 17, 2021 Non-Final Office Action dated Sep. 30, 2024.
U.S. Appl. No. 17/535,406, filed Nov. 24, 2021 Final Office Action dated Aug. 1, 2024.
U.S. Appl. No. 17/689,773, filed Mar. 8, 2022 Final Office Action dated Aug. 1, 2024.
U.S. Appl. No. 17/731,155 filed Apr. 27, 2022 Non-Final Office Action dated Aug. 22, 2024.
U.S. Appl. No. 18/141,289, filed Apr. 28, 2023 Non-Final Office Action dated Sep. 28, 2024.

(56)             References Cited

OTHER PUBLICATIONS

U.S. Appl. No. 18/524,620, filed Nov. 30, 2023 Notice of Allowance dated Sep. 12, 2024.

U.S. Appl. No. 17/529,022, filed Nov. 17, 2021 Notice of Allowance dated Jan. 2, 2025.

U.S. Appl. No. 17/529,022, filed Nov. 17, 2021 Restriction Requirement dated May 2, 2024.

U.S. Appl. No. 17/689,773, filed Mar. 8, 2022 Notice of Allowance dated Jan. 15, 2025.

U.S. Appl. No. 17/696,675, filed Mar. 16, 2022 Advisory Action dated Feb. 6, 2025.

U.S. Appl. No. 17/725,394, filed Apr. 20, 2022 Final Office Action dated Mar. 27, 2025.

U.S. Appl. No. 17/731,129, filed Apr. 27, 2022 Restriction Requirement dated Feb. 28, 2025.

U.S. Appl. No. 17/731,155 filed Apr. 27, 2022 Advisory Action dated Apr. 3, 2025.

U.S. Appl. No. 17/731,155, filed Apr. 27, 2022 Final Office Action dated Jan. 24, 2025.

U.S. Appl. No. 17/863,211, filed Jul. 12, 2022 Non-Final Office Action dated Jan. 29, 2025.

U.S. Appl. No. 17/945,875, filed Sep. 15, 2022 Non-Final Office Action dated Feb. 27, 2025.

U.S. Appl. No. 18/075,280, filed Dec. 5, 2022 Restriction Requirement dated Mar. 28, 2025.

U.S. Appl. No. 18/141,289, filed Apr. 28, 2023 Notice of Allowance dated Jan. 10, 2025.

U.S. Appl. No. 18/607,165, filed Mar. 15, 2024 Non-Final Office Action dated Jan. 15, 2025.

U.S. Appl. No. 18/607,165, filed Mar. 15, 2024 Notice of Allowance dated Apr. 3, 2025.

U.S. Appl. No. 17/696,675, filed Mar. 16, 2022 Notice of Allowance dated Jun. 17, 2025.

U.S. Appl. No. 17/717,919, filed Apr. 11, 2022 Non-Final Office Action dated Jul. 1, 2025.

U.S. Appl. No. 17/717,919, filed Apr. 11, 2022 Restriction Requirement dated Apr. 23, 2025.

U.S. Appl. No. 17/721,333, filed Apr. 14, 2022 Restriction Requirement dated May 6, 2025.

U.S. Appl. No. 17/725,394, filed Apr. 20, 2022 Advisory Action dated Jun. 5, 2025.

U.S. Appl. No. 17/725,394, filed Apr. 20, 2022 Non-Final Office Action dated Jun. 25, 2025.

U.S. Appl. No. 17/731,129, filed Apr. 27, 2022 Non-Final Office Action dated Apr. 28, 2025.

U.S. Appl. No. 17/731,155, filed Apr. 27, 2022 Non-Final Office Action dated Jul. 15, 2025.

U.S. Appl. No. 17/863,211, filed Jul. 12, 2022 Final Office Action dated Jun. 3, 2025.

U.S. Appl. No. 18/075,280, filed Dec. 5, 2022 Non-Final Office Action dated Jun. 11, 2025.

U.S. Appl. No. 17/721,333, filed Apr. 14, 2022 Non-Final Office Action dated Oct. 16, 2025.

U.S. Appl. No. 17/731,129, filed Apr. 27, 2022 Final Office Action dated Aug. 27, 2025.

U.S. Appl. No. 17/863,211, filed Jul. 12, 2022 Advisory Action dated Sep. 11, 2025.

U.S. Appl. No. 17/945,875, filed Sep. 15, 2022 Notice of Allowance dated Jul. 21, 2025.

U.S. Appl. No. 17/717,919 filed Apr. 11, 2022 Notice of Allowance dated Dec. 3, 2025.

U.S. Appl. No. 17/725,394 filed Apr. 20, 2022 Advisory Action dated Jan. 13, 2026.

U.S. Appl. No. 17/725,394 filed Apr. 20, 2022 Final Office Action dated Nov. 19, 2025.

U.S. Appl. No. 17/731,129 filed Apr. 27, 2022 Advisory Action dated Oct. 30, 2025.

U.S. Appl. No. 17/863,211 filed Jul. 12, 2022 Notice of Allowance dated Oct. 22, 2025.

U.S. Appl. No. 18/075,280 filed Dec. 5, 2022 Final Office Action dated Nov. 19, 2025.

* cited by examiner

SHAPE SENSING FIBER OPTIC TIP PROTECTION SYSTEMS AND DEVICES

BACKGROUND

Shape sensing optical fibers include shape sensing regions along the optical fiber. Sensors, such as fiber Bragg gratings, generate reflected light signals. In some instances, the sensing regions may extend to the proximity of the distal tip of the optical fiber. In some instances, the distal tip portion may become damaged during use causing a reduction in shape sensing capability. In some instances, the damage may include the end face of the optical fiber resulting in back scattering of light signals that may also cause a reduction in shape sensing capability.

Disclosed herein are fiber-optic tip protection devices and systems that address the foregoing.

SUMMARY

Briefly summarized, disclosed herein is a fiber-optic assembly for insertion within a patient body, that according to some embodiments, includes an optical fiber having a distal tip and a distal portion extending proximally away from the distal tip and a secondary mechanical layer extending around a circumference of the optical fiber along at least the distal portion of the optical fiber. The optical fiber includes a distal tip section configured to inhibit damage of the distal tip during use of the optical fiber, where the distal tip section (i) encompasses the distal tip, (ii) is disposed within the secondary mechanical layer, and (iii) includes a portion of the optical fiber disposed within a circuitous path, or an expansion of the optical fiber.

In some embodiments, the optical fiber includes a number of optical fiber cores, and one or more of the number of the optical fiber cores includes a number of sensors distributed along at least the distal portion of the optical fiber, where the sensors are configured to project reflected light signals proximally along the optical fiber based on a shape of the optical fiber.

In some embodiments, the secondary mechanical layer extends distally beyond the distal tip. The secondary mechanical layer may include a coil, tube or a combination of the coil and the tube.

In some embodiments, the assembly may further include a substance disposed within the secondary mechanical layer, where the substance defines a mechanical buffer between the optical fiber and the secondary mechanical layer. The substance may include an elastomeric material or a fluid. The secondary mechanical layer may include a closed distal end to facilitate containing the substance within the secondary mechanical layer. In some embodiments, the secondary mechanical layer may be coupled with the optical fiber so as to inhibit longitudinal displacement of the optical fiber with respect to the secondary mechanical layer.

In some embodiments, the secondary mechanical layer defines a circuitous path for disposition of the distal section therein. In such embodiments, the wherein the circuitous path may define a number of curved sections that include one or more of a spiral, a coil, a serpentine shape, a loop, a J-shape, or any combination thereof.

In some embodiments, the distal section includes an expansion (or expanded portion) defining a diameter that is greater than a diameter of the optical fiber. The expansion may be integrally formed of a material of the optical fiber or the expansion may be formed of an elastomeric material attached to the optical fiber. In some embodiments, the expansion is electrically conductive and, in some embodiments, the secondary mechanical layer is electrically conductive. In some embodiments, the expansion is electrically coupled with the secondary mechanical layer, and in some embodiments, the expansion extends beyond an open end of the secondary mechanical layer.

Also disclosed herein in is an elongate medical device, that according to some embodiments, includes an optical fiber assembly coupled with any one of a catheter, a stylet, a probe, or a guidewire. The optical fiber assembly includes an optical fiber defining a distal tip and a distal portion extending proximally away from the distal tip. The optical fiber assembly further includes a secondary mechanical layer extending around a circumference of the optical fiber along at least the distal portion of the optical fiber. The optical fiber includes a distal tip section configured to inhibit damage of the distal tip during use of the medical device assembly, where the distal tip section (i) encompasses the distal tip, (ii) is disposed within the secondary mechanical layer, and (iii) includes a portion of the optical fiber disposed within a circuitous path, or an expansion of the optical fiber.

In some embodiments, the optical fiber includes a number of optical fiber cores, where one or more of the number of the optical fiber cores includes a number of sensors distributed along at least a portion of the optical fiber, and the sensors are configured to project reflected light signals proximally along the optical fiber based on a shape of the at least a portion of the optical fiber.

In some embodiments, at least a subset of the number of sensors are distributed along the distal portion, where the distal portion includes the distal tip.

In some embodiments, the elongate medical device further includes a number of electrically conductive elements extending along the optical fiber, and the distal tip section includes an expansion formed of an electrically conductive material to define an electrode of the medical device, and where the electrode is coupled with at least one of the number electrically conductive elements.

These and other features of the concepts provided herein will become more apparent to those of skill in the art in view of the accompanying drawings and following description, which disclose particular embodiments of such concepts in greater detail.

BRIEF DESCRIPTION OF THE DRAWINGS

Embodiments of the disclosure are illustrated by way of example and not by way of limitation in the figures of the accompanying drawings, in which like references indicate similar elements and in which.

DETAILED DESCRIPTION

Figure 1:
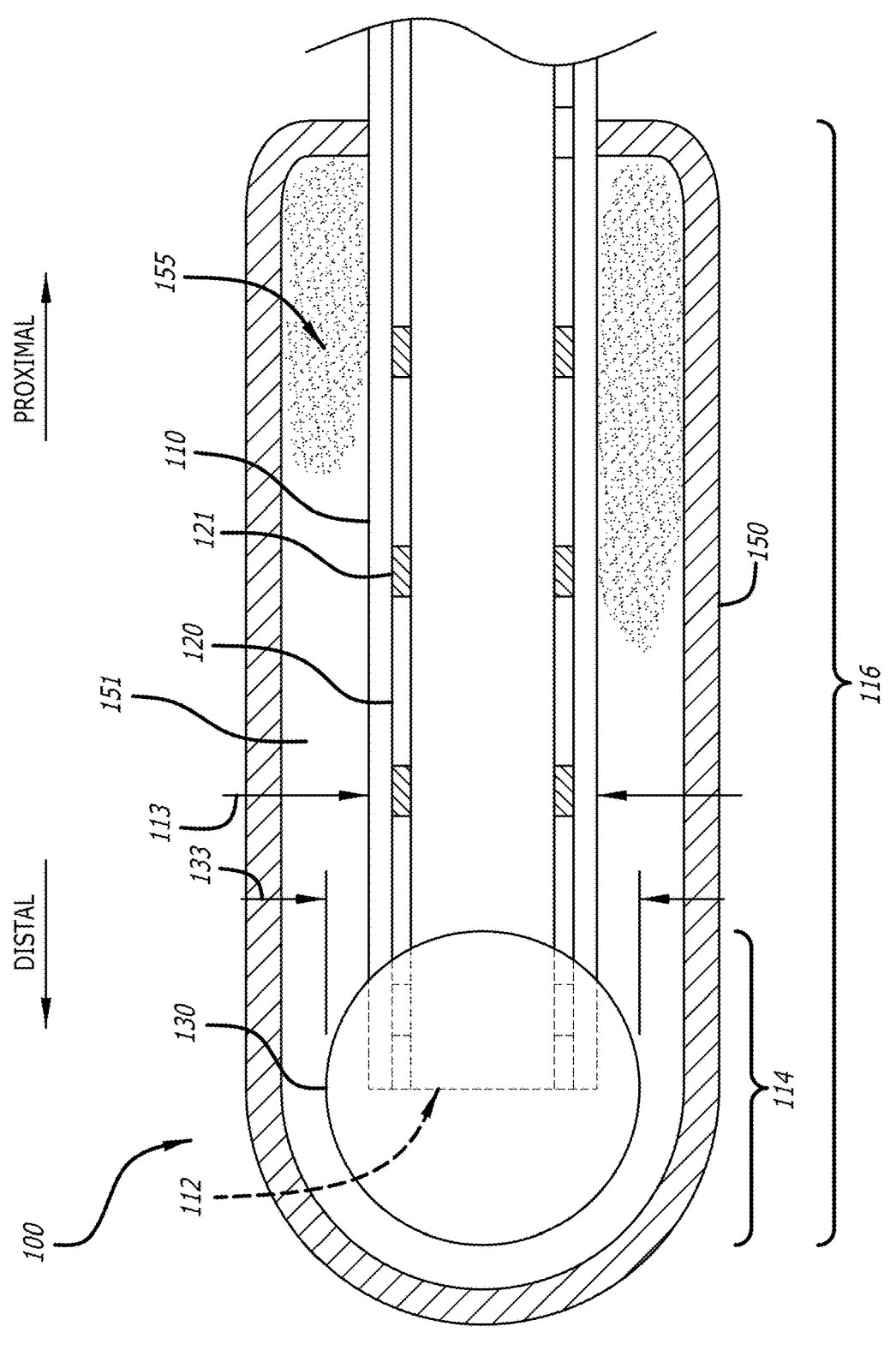
FIG. 1 is an illustration of a first embodiment of a fiber optic assembly, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

The terms "proximal" and "distal" refer to opposite directions of a medical device, including the devices disclosed herein. As used herein, the distal portion of a medical device is the portion nearest a patient during use. For example, the distal portion is defined as the portion of the device nearest to, or furthest inserted into, the patient. By way of further example, a component or feature extending proximally or in a proximal direction, extends away from the patient or in a direction toward an exterior of the patient.

The phrases "connected to," "coupled with," and "in communication with" refer to any form of interaction between two or more entities, including but not limited to mechanical, electrical, magnetic, electromagnetic, fluid, and thermal interaction. Two components may be coupled with each other even though they are not in direct contact with each other. For example, two components may be coupled with each other through an intermediate component.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations may be made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially straight" is recited with respect to a feature, it is understood that in further embodiments, the feature can have a precisely straight configuration.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Figure 2:
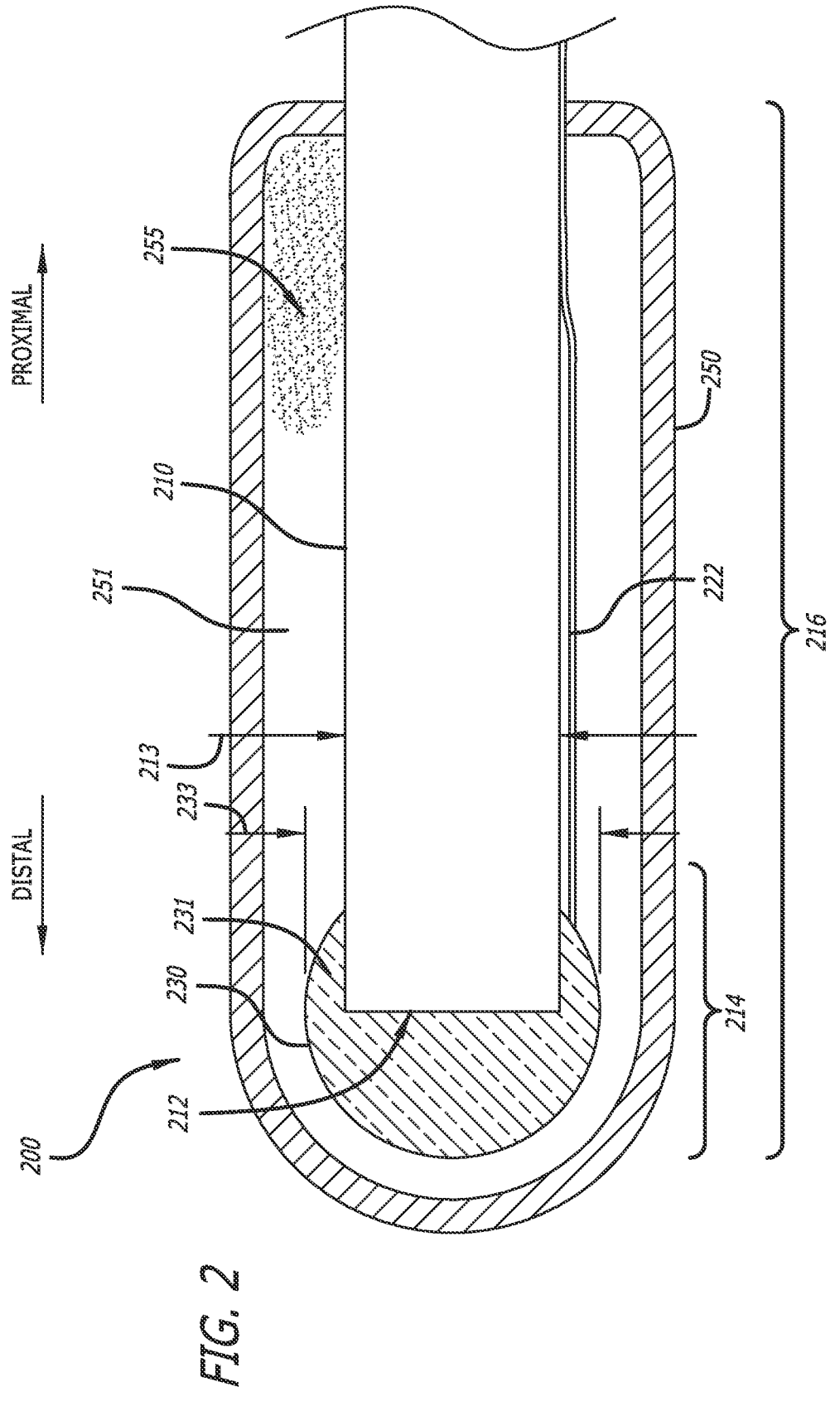
FIG. 2 is an illustration of a second embodiment of a fiber-optic assembly, in accordance with some embodiments.
Figure 3:
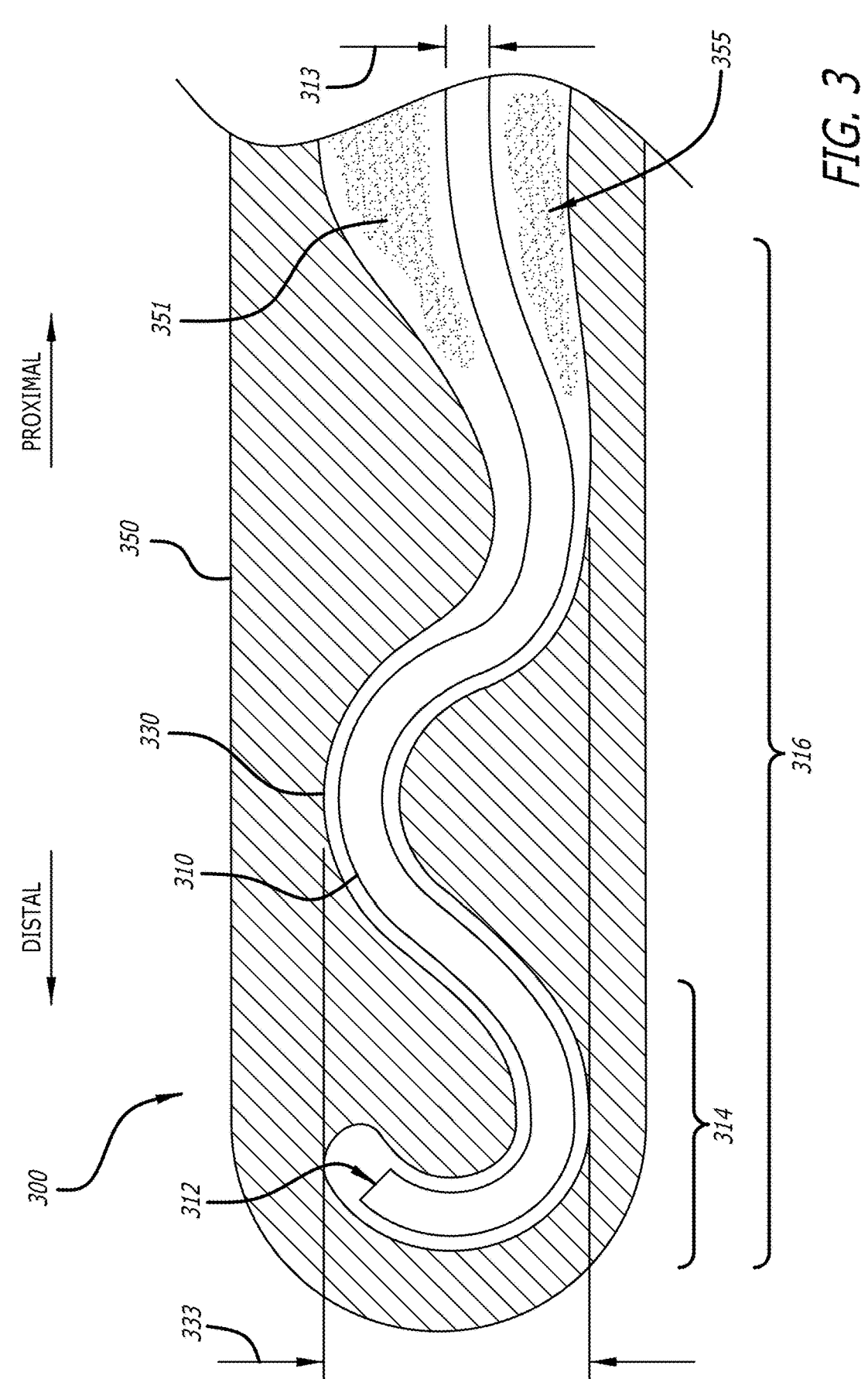
FIG. 3 is an illustration of a third embodiment of a fiber-optic assembly, in accordance with some embodiments.

FIGS. 1-3 illustrate different embodiments of a fiber-optic assembly, where the fiber optic assembly includes components and features that define a functionality of a fiber-optic tip protection system. Any of the fiber-optic assembly embodiments described herein below may be coupled with, incorporated into, or otherwise employed with another medical device to define a medical device assembly. In some embodiments, the other medical device may be any one of a catheter, a stylet, a probe, or a guidewire.

FIG. 1 is an illustration of a first embodiment of a fiber-optic assembly, in accordance with some embodiments. The fiber optic assembly generally includes components coupled with and/or integrally formed with an optical fiber along a distal portion of the optical fiber. In accordance with a first embodiment, the fiber-optic assembly (assembly) 100 includes an optical fiber 110 and a secondary mechanical layer 150 extending around a circumference of the optical fiber 110. The optical fiber 110 defines a distal tip 112, where the distal tip 112 defines the distal most end of at least a subset of optical operations of the optical fiber 110. In other words, at least one optical operation of the optical fiber 110 extends to the distal tip 112.

The optical fiber 110 may optionally be configured for shape sensing. In the illustrated embodiment, the optical fiber 110 includes a number (e.g., 1, 2, 3, 4, or more) of optical fiber cores 120, extending along a length of the optical fiber 110, that include a plurality of sensors (e.g., fiber Bragg gratings) 121 configured to project reflected light signals proximally along the optical fiber 110 based on a shape of the optical fiber 110.

The optical fiber 110 includes an expansion 130 disposed along a distal section 114 of the optical fiber 110 where the distal section 114 encompasses the distal tip 112. In the illustrated embodiment, the distal section 114 extends both proximally and distally in relation to the distal tip 112. However, in other embodiments, the distal section 114 may extend only proximally or only distally in relation to the distal tip 112.

The expansion 130 is configured to inhibit/prevent damage to the distal tip 112 during use of the optical fiber 110. The expansion 130 (or expanded portion) defines a diameter 133 that is greater than a diameter 113 of the optical fiber 110. The expansion 130 is formed of a material included with the optical fiber 110. In the illustrated embodiment, the expansion 130 includes a bulbous shape. In other embodiments, the expansion 130 may include other shapes, such as cylindrical, spherical, or teardrop shape, for example.

The secondary mechanical layer 150 is also configured to inhibit/prevent damage to the distal tip 112 during use of the optical fiber 110 in combination with the expansion 130. The secondary mechanical layer 150 may define an enhanced structural integrity to the optical fiber 110, such as a resistance to crushing, abrasion, or kinking, for example. In the illustrated embodiment, the secondary mechanical layer 150 is formed of a tube. In other embodiments, secondary mechanical layer 150 may be formed of a coil or a combination of the tube and the coil.

The secondary mechanical layer 150 may be disposed along a distal portion 116 of the optical fiber 110. The distal portion 116 generally extends proximally away from the distal tip 112. In some embodiments, the distal portion 116 may extend proximally away from the distal tip 112 a distance of about 1 mm, 2 mm, 4 mm, 8 mm, 16 mm, or more. The secondary mechanical layer 150 may also extended distally away from the distal tip 112. As such, the distal section 114 and the distal tip 112 may be included within the distal portion 116. In the illustrated embodiment, the secondary mechanical layer 150 includes a closed distal end. However, in other embodiments, the secondary mechanical layer 150 may include an open distal end.

The secondary mechanical layer 150 may be formed of a plastic, elastomeric, or metallic material. In some embodiments, the secondary mechanical layer 150 may be structurally formed defining a lumen 151 within which the optical fiber 110 may be subsequently inserted. In other embodiments, the secondary mechanical layer 150 may be formed onto the optical fiber 110, such as sprayed onto, over-molded onto, or otherwise applied to the optical fiber 110. In some embodiments, the secondary mechanical layer 150 may be attached to the optical fiber 110 so as to prevent longitudinal displacement of the secondary mechanical layer 150 with respect to the optical fiber 110. In some embodiments, the secondary mechanical layer 150, or more specifically a wall of the secondary mechanical layer 150, may define a fluid barrier. In some embodiments, the structure of the secondary mechanical layer 150 may be defined so as to allow the optical fiber 110 to flex/bend in accordance with the shape sensing operation of the optical fiber 110.

In some embodiments, the assembly 100 may include a buffering substance 155 disposed within the lumen 151 so as to occupy the annular space between the optical fiber 110 and the secondary mechanical layer 150. The buffering substance 155 may further inhibit/prevent damage to the distal tip 112 during use of the optical fiber 110 in combination with the expansion 130 and the secondary mechanical layer 150. The buffering substance 155 may include an elastomeric material or a fluid.

FIG. 2 is an illustration of a second embodiment of a fiber-optic assembly 200, in accordance with some embodiments, that can, in certain respects, resemble components of the fiber-optic assembly 100 described in connection with FIG. 1. It will be appreciated that all the illustrated embodiments may have analogous features. Accordingly, like features are designated with like reference numerals, with the leading digits incremented to "2." For instance, the optical fiber is designated as "110" in FIG. 1, and an analogous optical fiber is designated as "210" in FIG. 2. Relevant disclosure set forth above regarding similarly identified features thus may not be repeated hereafter. Moreover, specific features of the fiber-optic assembly 100 and related components shown in FIG. 1 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the fiber-optic assembly 100. Any suitable combination of the features, and variations of the same, described with respect to the fiber-optic assembly 100 and components illustrated in FIG. 1 can be employed with the fiber-optic assembly 200 and components of FIG. 2, and vice versa. This pattern of disclosure applies equally to further embodiments depicted in subsequent figures and described hereafter.

The fiber-optic assembly (assembly) 200 includes an optical fiber 210 and a secondary mechanical layer 250 extending around a circumference of the optical fiber 210. The optical fiber 210 defines a distal tip 212, where the distal tip 212 defines the distal most end of at least a subset of optical operations of the optical fiber 210. In other words, at least one optical functionality of the optical fiber 210 extends to the distal tip 212. The optical fiber 210 may optionally be configured for shape sensing.

The optical fiber 210 includes an expansion 230 coupled with the optical fiber 210 so as to encompasses the distal tip 212, where the expansion 230 is disposed along the distal section 214 of the optical fiber 210 where the distal section 214. In the illustrated embodiment, the distal section 214 extends both proximally and distally in relation to the distal tip 212.

The expansion 230 is configured to inhibit/prevent damage to the distal tip 212 during use of the optical fiber 210. The expansion 230 (or expanded portion) defines a diameter 233 that is greater than a diameter 213 of the optical fiber 210. The expansion 230 is formed of a compliant material 231, such as an elastomeric material. Exemplary elastomeric materials may include silicone, EPDM, natural rubber, and the like. In some embodiments, the compliant material 231 may be electrically conductive and as such, the expansion 230 may define an electrode configured for detecting electrical signals within a patient body.

The secondary mechanical layer 250 is also configured to inhibit/prevent damage to the distal tip 212 during use of the optical fiber 210 in combination with the expansion 230. The secondary mechanical layer 250 may define an enhanced structural integrity to the optical fiber 210, such as a resistance to crushing, abrasion, or kinking, for example. In the illustrated embodiment, the secondary mechanical layer 250 is formed of a tube. In other embodiments, secondary mechanical layer 250 may be formed of a coil or a combination of the tube and the coil.

The secondary mechanical layer 250 may be disposed along a distal portion 216 of the optical fiber 210. The distal portion 216 generally extends proximally away from the distal tip 212. In some embodiments, the distal portion 216 may extend proximally away from the distal tip 212 a distance of about 1 mm, 2 mm, 4 mm, 8 mm, 16 mm, or more. The secondary mechanical layer 250 may also extended distally away from the distal tip 212. As such, the distal section 214 and the distal tip 212 may be included within the distal portion 216. In the illustrated embodiment, the secondary mechanical layer 250 includes a closed distal end. However, in other embodiments, the secondary mechanical layer 250 may include an open distal end.

The secondary mechanical layer 250 may be formed of a plastic, elastomeric or metallic material. In some embodiments, the secondary mechanical layer 250 may be structurally formed defining a lumen 251 within which the optical fiber 210 may be subsequently inserted. In other embodiments, the secondary mechanical layer 250 may be formed onto the optical fiber 210, such as sprayed onto, over-molded onto, or otherwise applied to the optical fiber 210. In some embodiments, the secondary mechanical layer 250 may be attached to the optical fiber 210 so as to prevent longitudinal displacement of the secondary mechanical layer 250 with respect to the optical fiber 210. In some embodiments, the secondary mechanical layer 250, or more specifically a wall of the secondary mechanical layer 250, may define a fluid barrier. The structure of the secondary mechanical layer 250 may be defined so as to allow the optical fiber 210 to flex/bend in accordance with the shape sensing of the optical fiber 210.

In some embodiments, the assembly 200 may include a buffering substance 255 disposed within the lumen 251 so as to occupy the annular space between the optical fiber 210 and the secondary mechanical layer 250. The buffering substance 255 may further inhibit/prevent damage to the distal tip 212 during use of the optical fiber 210 in combination with the expansion 230 and the secondary mechanical layer 250. The substance may include an elastomeric material or a fluid. In some embodiments, the buffering substance 255 may be electrically conductive and may be electrically coupled with the expansion 230.

In some embodiments, the assembly 200 may include electrically conductive elements 222, such as wires, or traces, for example, extending along the optical fiber 210. The electrically conductive elements 222 may be electrically coupled with the expansion 230. As such, the electrically conductive elements 222 may be configured to receive electrical signals from the electrically conductive expansion 230 and transport the electrical signals proximally along the optical fiber assembly 200. As discussed above, the buffering substance 255 and/or the secondary mechanical layer 250 may be electrically conductive, and therefore, either or both of the buffering substance 255 and the secondary mechanical layer 250 may be configured to transport the electrical signals proximally along the optical fiber assembly 200.

FIG. 3 is an illustration of a third embodiment of a fiber optic assembly 300. The fiber-optic assembly (assembly) 300 includes an optical fiber 310 and a secondary mechanical layer 350 extending around a circumference of the optical fiber 310. The optical fiber 310 defines a distal tip 312, where the distal tip 312 defines the distal most end of at least a subset of optical operations of the optical fiber 310. In other words, at least one optical functionality of the optical fiber 310 extends to the distal tip 312. The optical fiber 310 may optionally be configured for shape sensing.

The optical fiber 310 is disposed with a circuitous path 330 along a distal section 314 of the optical fiber 310 where the distal section 314 encompasses the distal tip 312. In the illustrated embodiment, the distal section 314 extends distally in relation to the distal tip 312.

The secondary mechanical layer 350 is also configured to inhibit/prevent damage to the distal tip 312 during use of the optical fiber 310 in combination with the expansion 330. The secondary mechanical layer 350 may define an enhanced structural integrity to the optical fiber, such as a resistance to crushing, abrasion, or kinking, for example. The secondary mechanical layer 350 may be disposed along a distal portion 316 of the optical fiber 310. The distal portion 316 generally extends proximally away from the distal tip 312. In some embodiments, the distal portion 316 may extend a proximally away from the distal tip 312 a distance of about 1 mm, 2 mm, 4 mm, 8 mm, 16 mm, or more. The secondary mechanical layer 350 may also extended distally away from the distal tip 312. As such, the distal section 314 may be included within the distal portion 316. In the illustrated embodiment, the secondary mechanical layer 350 includes a closed distal end. However, in other embodiments, the secondary mechanical layer 350 may include an open distal end.

The secondary mechanical layer 350 defines the circuitous path 330. In the illustrated embodiment, the circuitous path 330 defines a diameter (lateral dimension) 333 of the optical fiber 310 along the distal section 314, where the diameter 333 is greater than the diameter 313 of the optical fiber 310. In other embodiments, the circuitous path 330 may be substantially straight, such that the diameter 333 is similar to the diameter 313. In the illustrated embodiments, the circuitous path 330 may define a serpentine shape. In other embodiments, the circuitous path 330 may define a different shape, such as a spiral, a coil, a loop, a J-shape, or any combination thereof, for example. In some embodiments, the circuitous path 330 may be disposed within a single plane, i.e., a single lateral dimension with respect to a longitudinal axis of the secondary mechanical layer 350. In other embodiments, the circuitous path 330 may extend in both lateral dimensions with respect to the longitudinal axis.

The secondary mechanical layer 350 may be formed of a plastic, elastomeric, or metallic material. In some embodiments, the secondary mechanical layer 350 may be structurally formed defining a lumen 351 which defines the circuitous path 330 along the distal section 314. In some embodiments, the secondary mechanical layer 350 may be attached to the optical fiber 310 so as to prevent longitudinal displacement of the secondary mechanical layer 350 with respect to the optical fiber 310.

The secondary mechanical layer 350 may be formed of a single component or multiple components. For example, secondary mechanical layer 350 may be formed of a solid material having the circuitous path 330 formed therein, according to some embodiments. In other embodiments, the secondary mechanical layer 350 may include (i) an outer wall, such as a tube or a coil, for example, defining the lumen 351 and (ii) a buffering substance 355 disposed within the lumen 351, where the circuitous path 330 extends through the buffering substance 355. The buffering substance 355 substance may include an elastomeric material. In some embodiments, the assembly 300 may be assembled by first defining the circuitous path 330 and then inserting the optical fiber 310 therein. In other embodiments, the assembly 300 may be assembled by (i) forming a circuitous shape of the optical fiber 310, (ii) placing the circuitous shape of the optical fiber 310 in the lumen 351, and (iii) filling the lumen 351 with the buffering substance 355.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A fiber-optic assembly for insertion within a patient body, comprising:
   a shape sensing optical fiber defining a distal portion comprising a distal section of the optical fiber, the distal section including an optical fiber tip; and
   a secondary mechanical layer extending around a circumference of the optical fiber along at least the distal portion of the optical fiber, the secondary mechanical layer including a distal end disposed distal the optical fiber, wherein:
   the distal section is disposed within the secondary mechanical layer,
   the distal section includes a portion of the optical fiber disposed within a circuitous path defined with respect to the secondary mechanical layer, the circuitous path configured to inhibit damage of the optical fiber tip during use of the optical fiber, and
   a portion of the distal section extends distally away from the optical fiber tip toward the distal end of the secondary mechanical layer.

2. The assembly of claim 1, wherein:
   the optical fiber includes a plurality of optical fiber cores;
   one or more of the plurality of the optical fiber cores includes a plurality of sensors distributed along at least the distal portion of the optical fiber; and
   the sensors are configured to project reflected light signals proximally along the optical fiber based on a shape of the optical fiber.

3. The assembly of claim 1, wherein the secondary mechanical layer is formed of a tube.

4. The assembly of claim 1, further comprising a substance filling an annular space between the optical fiber and the secondary mechanical layer, the substance defining a mechanical buffer between the optical fiber and the secondary mechanical layer.

5. The assembly of claim 4, wherein the substance includes an elastomeric material.

6. The assembly of claim 4, wherein the substance includes a fluid.

7. The assembly of claim 1, wherein the distal end of the secondary mechanical layer includes a closed distal end.

8. The assembly of claim 1, wherein the secondary mechanical layer is coupled with the optical fiber so as to inhibit longitudinal displacement of the optical fiber with respect to the secondary mechanical layer.

9. The assembly of claim 1, wherein the circuitous path includes a spiral, a coil, a serpentine shape, a loop, a J-shape, or any combination thereof.

10. An elongate medical device assembly, comprising:
a shape sensing optical fiber assembly coupled with any one of a catheter, a stylet, a probe, or a guidewire, the optical fiber assembly comprising:
an optical fiber defining an optical fiber tip and a distal portion extending proximally away from the optical fiber tip; and
a secondary mechanical layer extending around a circumference of the optical fiber along at least the distal portion of the optical fiber, the secondary mechanical layer including a distal end disposed distal the optical fiber, wherein:
the distal section is disposed within the secondary mechanical layer,
the distal section includes a portion of the optical fiber disposed within a circuitous path defined with respect to the secondary mechanical layer, the circuitous path configured to inhibit damage of the optical fiber tip during use of the optical fiber, and
a portion of the distal section extends distally away from the optical fiber tip toward the distal end of the secondary mechanical layer.

11. The elongate medical assembly of claim 10, wherein:
the optical fiber includes a plurality of optical fiber cores;
one or more of the plurality of the optical fiber cores includes a plurality of sensors distributed along at least a portion of the optical fiber; and
the sensors are configured to project reflected light signals proximally along the optical fiber based on a shape of the at least a portion of the optical fiber.

12. The elongate medical assembly of claim 11, wherein at least a subset of the plurality of sensors are distributed along the distal portion, the distal portion including the optical fiber tip.

* * * * *